United States Patent
Wang et al.

(10) Patent No.: US 12,207,733 B2
(45) Date of Patent: Jan. 28, 2025

(54) ADJUSTABLE BED WITH NO HINGING CONNECTIONS OF PLATFORMS

(71) Applicant: Nisco Co., Ltd, Jiangsu (CN)

(72) Inventors: Wei Wang, Jiangsu (CN); Fahuan Zhang, Jiangsu (CN); Jian Xie, Jiangsu (CN); Yifan Mao, Jiangsu (CN)

(73) Assignee: NISCO CO., LTD, Jiangsu (CN)

( * ) Notice: Subject to any disclaimer, the term of this patent is extended or adjusted under 35 U.S.C. 154(b) by 292 days.

(21) Appl. No.: 17/963,277

(22) Filed: Oct. 11, 2022

(65) Prior Publication Data

US 2023/0033335 A1 Feb. 2, 2023

Related U.S. Application Data

(63) Continuation-in-part of application No. 16/990,085, filed on Aug. 11, 2020, now Pat. No. 11,602,228.

(60) Provisional application No. 62/889,145, filed on Aug. 20, 2019.

(30) Foreign Application Priority Data

Oct. 14, 2021 (CN) .......................... 202122485087.4

(51) Int. Cl.
| | |
|---|---|
| *A47C 20/00* | (2006.01) |
| *A47C 20/04* | (2006.01) |
| *A47C 21/00* | (2006.01) |
| *A47C 31/00* | (2006.01) |
| *A61M 21/02* | (2006.01) |
| *A61M 21/00* | (2006.01) |

(52) U.S. Cl.
CPC .......... *A47C 20/041* (2013.01); *A47C 21/006* (2013.01); *A47C 31/005* (2013.01); *A47C 31/008* (2013.01); *A61M 21/02* (2013.01); *A61M 2021/0016* (2013.01); *A61M 2021/0066* (2013.01); *A61M 2205/3553* (2013.01)

(58) Field of Classification Search
CPC ... A47C 20/041; A47C 21/006; A47C 31/005; A47C 20/00; A47C 20/04; A61M 21/02; A61M 2021/0016; A61M 2021/0066; A61M 2205/3553
See application file for complete search history.

(56) References Cited

U.S. PATENT DOCUMENTS

| | | | | | |
|---|---|---|---|---|---|
| 4,996,731 | A | * | 3/1991 | Kruyt | A47C 20/041 5/618 |
| 5,645,578 | A | * | 7/1997 | Daffer | A61M 21/0094 600/27 |
| 6,006,379 | A | * | 12/1999 | Hensley | A47C 20/08 5/915 |
| 6,826,793 | B2 | * | 12/2004 | Tekulve | A61G 7/015 5/81.1 R |

(Continued)

*Primary Examiner* — Fredrick C Conley
(74) *Attorney, Agent, or Firm* — Locke Lord LLP; Tim Tingkang Xia, Esq.

(57) ABSTRACT

An adjustable bed includes a frame structure; an upper support bracket and a lower support bracket pivotally connected to the frame structure; a plurality of platforms disposed on the frame structure and supported by the upper support bracket and the lower support bracket without using hinging means; and an adjustable assembly coupled with the frame structure and the upper support bracket and the lower support bracket for operably adjusting one or more of the plurality of platforms in desired positions.

16 Claims, 10 Drawing Sheets

(56) References Cited

U.S. PATENT DOCUMENTS

2008/0262657 A1* 10/2008 Howell ................ A47C 20/041
                                                    700/275
2008/0276373 A1* 11/2008 Clenet .................. A47C 21/026
                                                      5/618
2014/0366267 A1* 12/2014 Suh ...................... A47C 20/041
                                                      5/174
2016/0206113 A1*  7/2016 Rawls-Meehan .... A47C 20/048

* cited by examiner

ADJUSTABLE BED WITH NO HINGING CONNECTIONS OF PLATFORMS

CROSS-REFERENCE TO RELATED PATENT APPLICATIONS

This application is a continuation-in-part application of U.S. patent application Ser. No. 16/990,085, filed Aug. 11, 2020, now U.S. Pat. No. 11,602,228, which itself claims priority to and the benefit of U.S. Provisional Patent Application Ser. No. 62/889,145, filed Aug. 20, 2019, which are incorporated herein in their entireties by reference.

This application also claims priority to and the benefit of Chinese Patent Application No. 202122485087.4, filed Oct. 14, 2021, which is incorporated herein in its entirety by reference.

FIELD OF THE INVENTION

The invention generally relates to a bed, and more particular to an adjustable bed with no hinging connections of platforms and/or an aromatherapy system.

BACKGROUND OF THE INVENTION

Sleep is critical for people in every aspect of their lives. Beds are necessary furniture for people to sleep on. In a conventional adjustable bed, platforms (bed boards) are directly hinged to one another through hinges. It is known that in this design the hinges bear a large bearing capacity. Once the hinges have problems, it will bring safety problems, thereby potential safety hazards. On the other hand, the hinge structure is complex, which may make the installation, transportation, and/or maintenance of the adjustable bed is more troublesome. Thus, it is beneficial and desirable for people to have a bed system that is easy for installation, transportation, and/or maintenance. In addition, it is also beneficial and desirable that the bed system has therapeutic functions to promote health and well-being of a user.

SUMMARY OF THE INVENTION

The invention, in one aspect, relates to an adjustable bed. The adjustable bed comprises a frame structure; an upper support bracket and a lower support bracket pivotally connected to the frame structure; a plurality of platforms disposed on the frame structure and supported by the upper support bracket and the lower support bracket without using hinging means; and an adjustable assembly coupled with the frame structure and the upper support bracket and the lower support bracket for operably adjusting one or more of the plurality of platforms in desired positions.

In one embodiment, the frame structure comprises a pair of side rails transversely spaced and longitudinally extended and being parallel to each other, each side rail having an upper end and opposite, lower end; an upper rail and a lower rail longitudinally spaced and transversely extended, two ends of the upper rail connected to the upper ends of the pair of side rails and two ends of the lower rail connected to the lower ends of the pair of side rails such that the upper rail and the lower rail are parallel to each other; and an upper reinforcement beam and a lower reinforcement beam directly and fixedly connected to each of the pair of side rails at positons such that the upper reinforcement beam is positioned between the upper rails and the lower reinforcement beam, while the lower reinforcement beam is positioned between the upper reinforcement beam and the lower rail. As such, the pair of side rails, the upper rail, the lower rail, the upper reinforcement beam and the lower reinforcement beam of the frame structure are co-planar in a rectangle form.

In one embodiment, the upper support bracket comprises a pair of back support bars pivotally connected to the upper reinforcement beam; and the lower support bracket comprises a pair of lower support structures, each lower support structure comprising a thigh support bar pivotally connected to the lower reinforcement beam, and a leg support bar pivotally connected to the thigh support bar, and a limit bar pivotally connected to the leg support bar and a respective side rail of the pair of side rails.

In one embodiment, the plurality of platforms comprises a back platform mounted on the back support bar of the back support bar bracket; a seat platform mounted on the side rails of the frame structure; a thigh platform mounted on the thigh support bar of the leg support bracket; and a leg platform mounted on the leg support bar of the leg support bracket. The back platform, the seat platform, the thigh platform and the leg platform are not hinged to one another.

In one embodiment, each of the back support bar, the thigh support bar, and the leg support bar has one or more mounting holes for mounting the back platform, the thigh platform and the leg platform, respectively.

In one embodiment, each back support bar has a sliding slot formed thereunderneath; and each thigh support bar has a sliding slot formed thereunderneath.

In one embodiment, the adjustable assembly comprises a back lifting assembly comprising a back lifting bracket pivotally connected to the frame structure and slidably coupled to the upper support bracket, and a back lifting actuator pivotally connected between the back lifting bracket and the frame structure for operably driving the back lifting bracket to pivotally move in an upward rotating direction or a downward rotating direction relative to the frame structure; and a leg lifting assembly comprising a leg lifting bracket pivotally connected to the frame structure and slidably coupled to the lower support bracket, and a leg lifting actuator pivotally connected between the leg lifting bracket and the frame structure for operably driving the leg lifting bracket to pivotally move in an upward rotating direction or a downward rotating direction relative to the frame structure.

In one embodiment, the back lifting bracket comprises a middle bar and a pair of swing arms, wherein the pair of swing arms is transversely spaced and rigidly connected to ends of the transversely extending middle bar, and each of the pair of swing arms has a first end portion and an opposite, second end portion, wherein the first end portion of each swing arm is pivotally mounted to a respective side rail of the frame structure; and the back lifting actuator comprises a motor member, an outer tube extending from the motor member, an activation rod received in the outer tube, engaged with the motor member and configured to be telescopically movable relative to the outer tube according to a direction of motor rotation, wherein the motor member is pivotally connected to the upper rail of the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the upper rail of the frame structure.

In one embodiment, the swing arms are in an arc-shaped design.

In one embodiment, the second end portion of the swing arms is equipped with a back lifting wheel, which is operably slidable along the sliding slot of the back support bar of the upper support bracket.

In one embodiment, the leg lifting bracket comprises a middle bar and a pair of swing arms, wherein the pair of swing arms is transversely spaced and rigidly connected to ends of the transversely extending middle bar, and each of the pair of swing arms has a first end portion and an opposite, second end portion, wherein the first end portion of each swing arm is pivotally mounted to a respective side rail of the frame structure; and the leg lifting actuator comprises a motor member, an outer tube extending from the motor member, an activation rod received in the outer tube, engaged with the motor member and configured to be telescopically movable relative to the outer tube according to a direction of motor rotation, wherein the motor member is pivotally connected to the lower rail of the frame structure, and the activation rod has a distal end portion pivotally connected to the middle bar of the leg lifting bracket, or wherein the motor member is pivotally connected to the middle bar of the leg lifting bracket, and the activation rod has a distal end portion pivotally connected to the lower rail of the frame structure.

In one embodiment, the second end portion of the swing arms is equipped with a leg lifting wheel, which is operably slidable along the sliding slot of the thigh support bar of the lower support bracket.

In one embodiment, each of the pair of side rails comprises two parts that are foldably connected to each other by a folding mechanism.

In one embodiment, the adjustable bed further comprises an aromatherapy system attached onto the one or more platforms for producing desired fragrance in a surrounding space of the adjustable bed so as to promote health and well-being of a user.

In one embodiment, the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

In one embodiment, each aromatherapy device has one or more working modes, wherein the one or more working modes comprises a first working mode in which said aromatherapy device is turned on or turned off based on the user's instruction; a second working mode in which said aromatherapy device is turned on for a first period of time, and then turned off; and a third working mode in which said aromatherapy device is turned on for a second period of time regularly in a third period of time.

In one embodiment, each aromatherapy device comprises a container for containing an aromatic substance; a diffuser coupled to the container for operably heating the aromatic substance therein so as to produce the fragrance; and one or more indicators, each indicator for indicating one of the one or more working modes of said aromatherapy device.

In one embodiment, each aromatherapy device is controllable to operate in one of the one or more working modes by a remote control or an APP.

In one embodiment, the adjustable bed further comprises at least one massage assembly for providing massage effects to the user.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
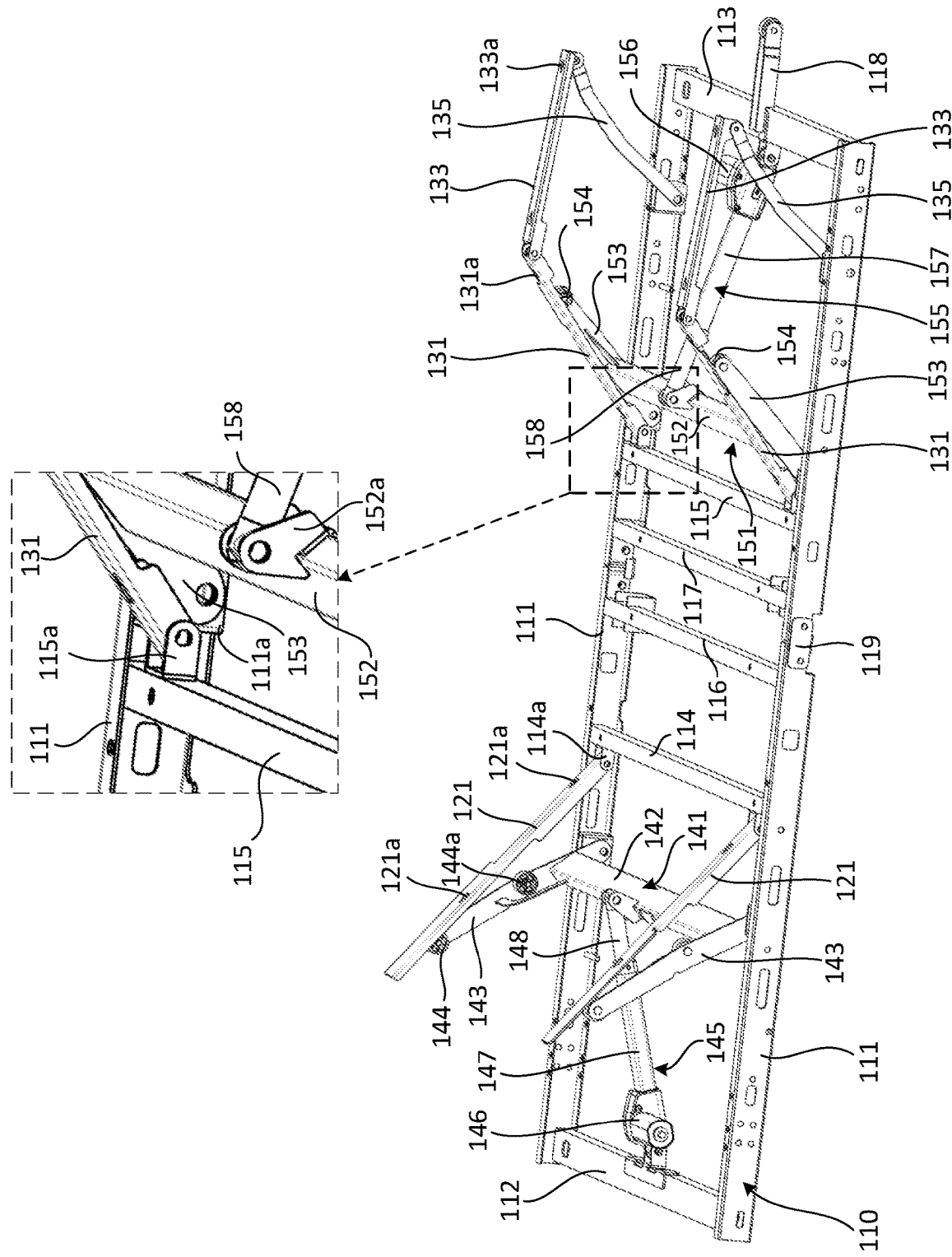
FIG. 1 shows schematically and partially a front perspective view of an adjustable bed according to one embodiment of the invention. The adjustable bed is in an adjusting/lifting state.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about" "substantially" or "approximately" can be inferred if not expressly stated.

The term "APP", used herein the specification, refers to an application, especially as downloaded by a user to and installed in a mobile device, which a software program that is designed to perform specific functions directly for the user or, in some cases, for another application program or for operations of devices, such as a back lifting actuator (motor), a leg lifting actuator (motor), an aromatherapy system, and/or a massage assembly in the invention. The term "platform" used herein refers to a board, bed board, panel, deck panel, or deck board.

As used in this specification, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. In accordance with the purposes of this invention, as embodied and broadly described herein, this invention, in one aspect, relates to an adjustable bed without hinging connections of platforms or bed boards Exemplary embodiments of the invention will be described in conjunction with the accompanying drawings in FIGS. 1-11. For purposes of clarity, the same reference numbers will be used in the drawings to identify similar elements.

Referring to FIGS. 1-7, the adjustable bed 100 includes a frame structure 110; an upper support bracket 120 and a lower support bracket 130 pivotally connected to the frame structure 110; a plurality of platforms 180 disposed on the frame structure and supported by the upper support bracket and the lower support bracket without using hinging means for connection; and an adjustable assembly coupled with the frame structure and the upper support bracket and the lower support bracket for operably adjusting one or more of the plurality of platforms in desired positions.

Specifically, the frame structure 110 comprises a pair of side rails 111 transversely spaced and longitudinally extended and being parallel to each other. Each side rail 111 has an upper end, and an opposite, lower end.

The frame structure 110 also comprises an upper rail 112 and a lower rail 113 longitudinally spaced and transversely extended. Two ends of the upper rail 112 are connected to the upper ends of the pair of side rails 111, and two ends of the lower rail 113 are connected to the lower ends of the pair of side rails 111, such that the upper rail 112 and the lower rail 113 are parallel to each other, as shown in FIG. 1 for example. Preferably, the connections of the pair of side rails 111 to the upper and lower rails 112 and 113 are by welding ends of the upper rail 112 onto end portions of the pair of side rails 111, and welding ends of the lower rail 114 onto opposite end portions of the pair of side rails 111. Other connecting means can also be utilized to practice the invention.

The frame structure 110 further comprises an upper reinforcement beam 114 and a lower reinforcement beam 115 directly and fixedly connected to each of the pair of side rails 111 at positons such that the upper reinforcement beam 114 is positioned between the upper rails 112 and the lower reinforcement beam 115, while the lower reinforcement beam 115 is positioned between the upper reinforcement beam 114 and the lower rail 113. Preferably, the direct and fixed connections of the upper and lower reinforcement beams 114 and 115 to the pair of side rails 111 are by welding ends of the upper and lower reinforcement beams 114 and 115 onto positions of the pair of side rails 111. Other connecting means can also be utilized to practice the invention. Further, as shown in FIG. 1, additional reinforcement beams such as beams 116 and 117 may be provided between the upper and lower reinforcement beams 114 and 115 for further reinforcement.

As such, the pair of side rails 111, the upper rail 112, the lower rail 113, the upper reinforcement beam 114 and the lower reinforcement beam 115 of the frame structure 110 are co-planar in a rectangle form, as shown in FIG. 1.

In addition, each of the pair of side rails 111 may comprise two parts that are foldably connected to each other by a folding mechanism 119. Please refer to the disclosure of U.S. patent application Ser. No. 16/990,085, which is incorporated herein in its entirety by reference, for details of the folding mechanism 119, which is not repeated herein.

The upper support bracket 120 comprises a pair of back support bars 121, each of which is pivotally connected to the upper reinforcement beam 114 via a bracket 114a mounted onto the upper reinforcement beam 114, as shown in FIG. 1. Each back support bar 121 has a sliding slot 122 formed thereunderneath, i.e., on its lower (bottom) side, as shown in FIG. 2.

The lower support bracket 130 comprises a pair of lower support structures. Each lower support structure comprises a thigh support bar 131, a leg support bar 133 and a limit bar 135, each of which has a first end and an opposite, second end. The first end of the thigh support bar 131 is pivotally connected to the lower reinforcement beam 115 via a bracket 115a mounted onto the lower reinforcement beam 115, and the second end of the thigh support bar 131 is pivotally connected to the first end of the leg support bar 133. The second end of the leg support bar 133, in turn, is pivotally connected to the first end of the limit bar 135. The second end of the limit bar 135 is pivotally connected to a respective side rail of the pair of side rails 111.

Figure 2:
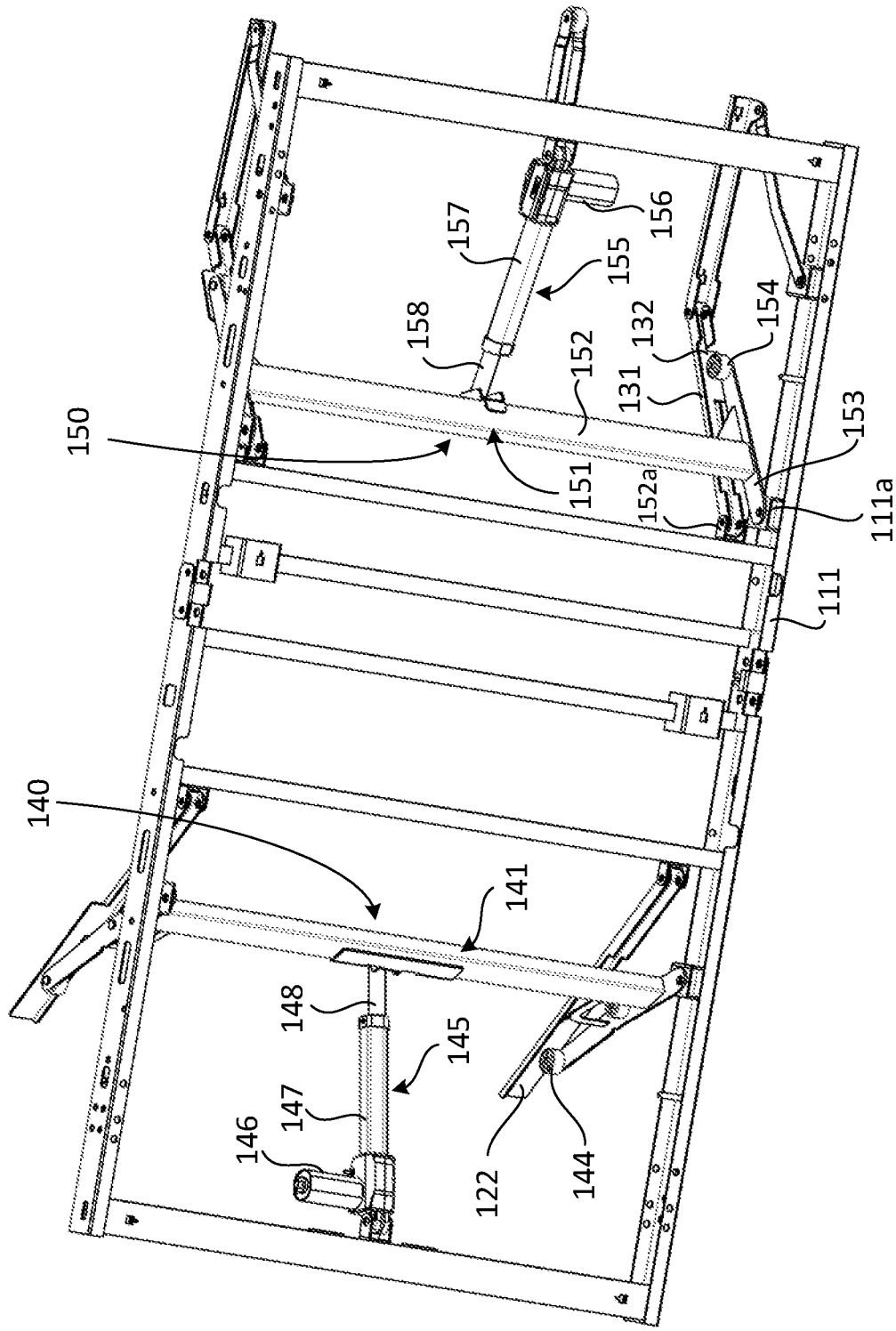
FIG. 2 shows schematically and partially a rear perspective view of the adjustable bed shown in FIG. 1.

In one embodiment, each thigh support bar 131 has a sliding slot 132 formed thereunderneath, i.e., on its lower (bottom) side, as shown in FIG. 2.

The plurality of platforms 180 comprises a back platform 181 mounted on the back support bar 121 of the back support bar bracket 120; a seat platform 182 mounted on the side rails 111 of the frame structure 110; a thigh platform 183 mounted on the thigh support bar 131 of the leg support bracket 130; and a leg platform 184 mounted on the leg support bar 133 of the leg support bracket 130. In some embodiments each of the back support bar 121, the thigh support bar 131, and the leg support bar 133 has one or more mounting holes, e.g., 121a, 131a or 133a shown in FIG. 1, for mounting the back platform 181, the thigh platform 183 and the leg platform 184 onto the back support bar 121, the thigh support bar 131 and the leg support bar 133, respectively. Practically, each of the back platform 181, the thigh platform 183 and the leg platform 184 may have one or more installation holes 26, which are corresponding to the one or more mounting holes 121a, 131a or 133a of the back support bar 121, the thigh support bar 131 or the leg support bar 133. As such, a user can easily install the bed by placing screws or nuts or other connection means into the installation holes of the platforms and the mounting holes of the back support bar 121, the thigh support bar 131 and the leg support bar 133.

In addition, each of the back platform 181, the thigh platform 183, and the leg platform 184 may have massage receiving slots 25 for accommodating massage devices, and/or openings 24 for avoiding the back and leg lifting actuators 145 and 155 from being in contact with these platforms during the movements of the back and leg lifting actuators 145 and 155.

Accordingly, the back platform 181, the seat platform 182, the thigh platform 183 and the leg platform 184 are not hinged to one another. In other words, there is devoid of any hinges between the back platform 181, the seat platform 182, the thigh platform 183 and the leg platform 184.

The adjustable assembly includes a back lifting assembly 140 and a leg lifting assembly 150.

The back lifting assembly 140 includes a back lifting bracket 141 pivotally connected to the frame structure 110 and slidably coupled to the upper support bracket 120, and a back lifting actuator 145 pivotally connected between the back lifting bracket 141 and the frame structure 110 for operably driving the back lifting bracket 141 to pivotally move in an upward rotating direction or a downward rotating direction relative to the frame structure 110.

In some embodiments, the back lifting bracket 141 comprises a middle bar 142 and a pair of swing arms 143. The pair of swing arms 143 is transversely spaced and rigidly connected to ends of the transversely extending middle bar 142 in an H-shaped form. Each of the pair of swing arms 143 has a first end portion and an opposite, second end portion. The first end portion of each swing arm 143 is pivotally mounted to a respective side rail 111 of the frame structure 110. The second end portion of each swing arm 143 is equipped with a back lifting wheel/roller 144, which is operably slidable along the sliding slot 122 of the back support bar 121 of the upper support bracket 120. In some embodiments the second end portion of each swing arms 143 may also be equipped with the first lifting wheel/roller 144 and the second lifting wheel 144a. In addition, each of the pair of swing arms 143 may be reinforced by a reinforcing piece rigidly connected to the middle bar 143 and the swing arm 143.

In some embodiments, the swing arms 143 are in an arc-shaped design.

The back lifting actuator 145 comprises a motor member 146, an outer tube 147 extending from the motor member 146, an activation rod 148 received in the outer tube 147, engaged with the motor member 146 and configured to be telescopically movable relative to the outer tube 147 according to a direction of motor rotation. In one embodiment, the motor member 146 is pivotally connected to the upper rail 112 of the frame structure 110, and the activation rod 148 has a distal end portion pivotally connected to the middle bar 142 of the back lifting bracket 141. In another embodiment, the motor member 146 is pivotally connected to the middle bar 142 of the back lifting bracket 140, and the activation rod 148 has a distal end portion pivotally connected to the upper rail 112 of the frame structure 110.

Figure 4:
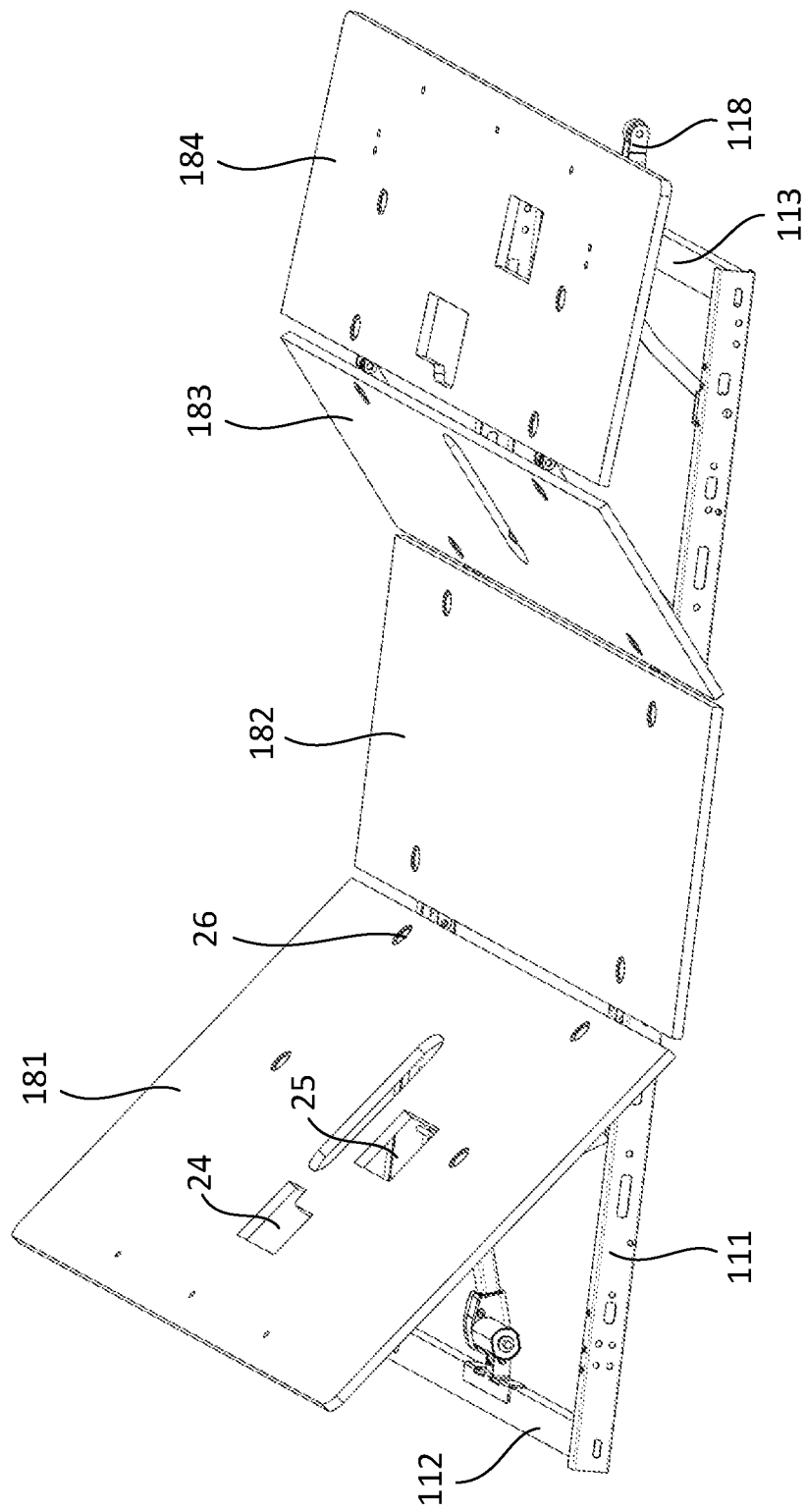
FIG. 4 shows schematically a front perspective view of the adjustable bed shown in FIG. 1. The adjustable bed is in the adjusting/lifting state.
Figure 5:
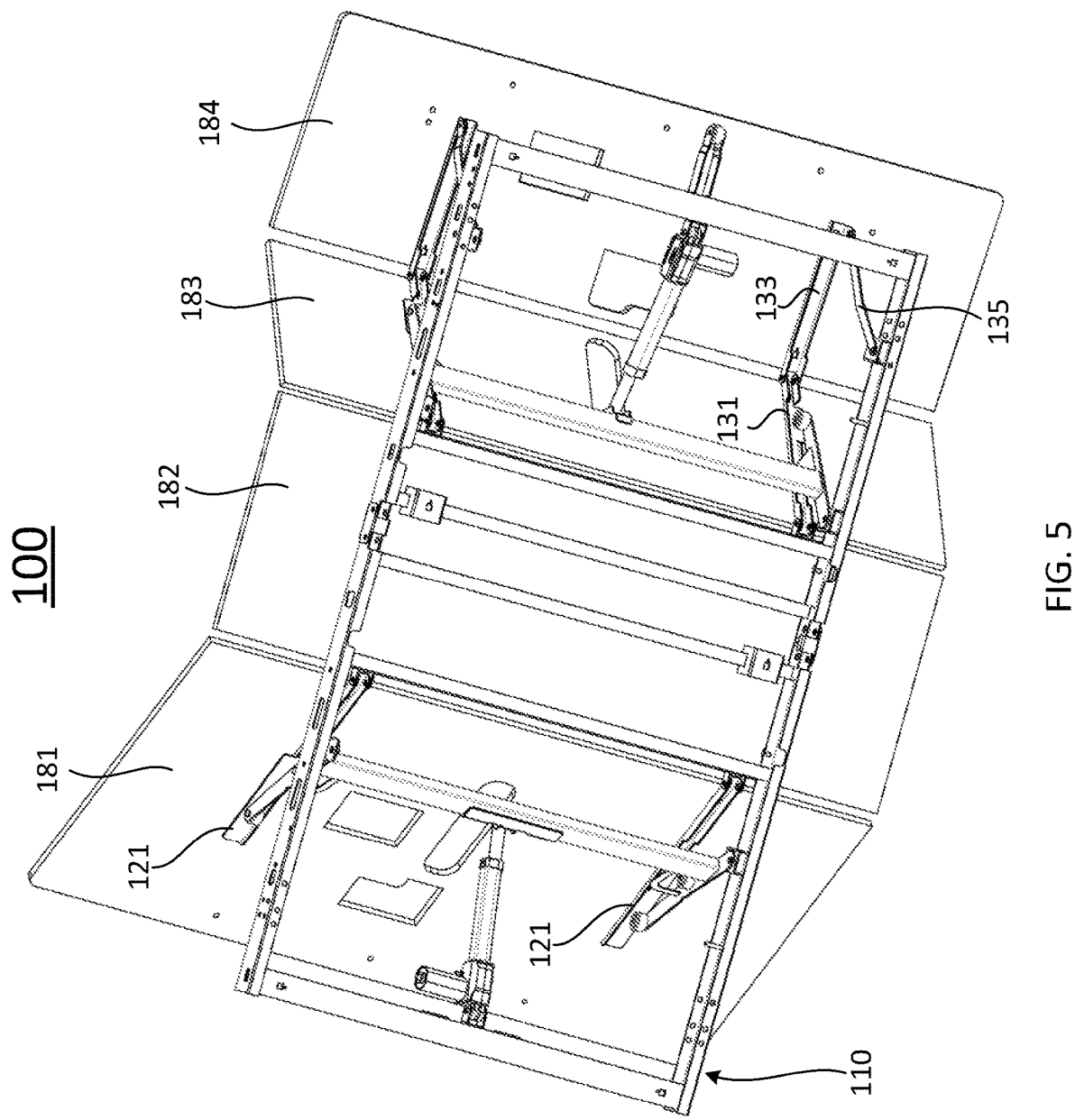
FIG. 5 shows schematically a rear perspective view of the adjustable bed shown in FIG. 1.
Figure 6:
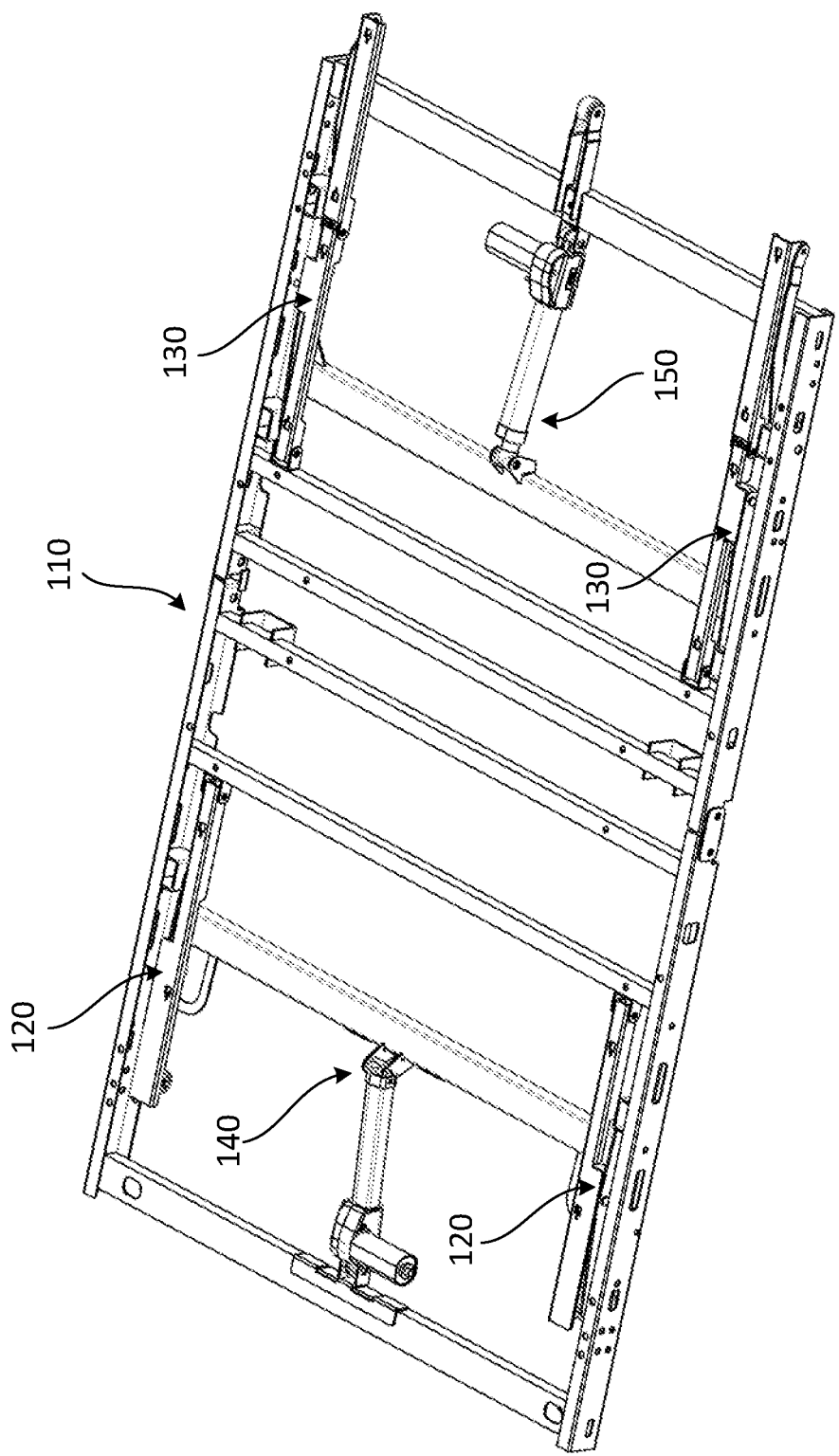
FIG. 6 shows schematically and partially a front perspective view of the adjustable bed shown in FIG. 1. The adjustable bed is in a flat state.
Figure 7:
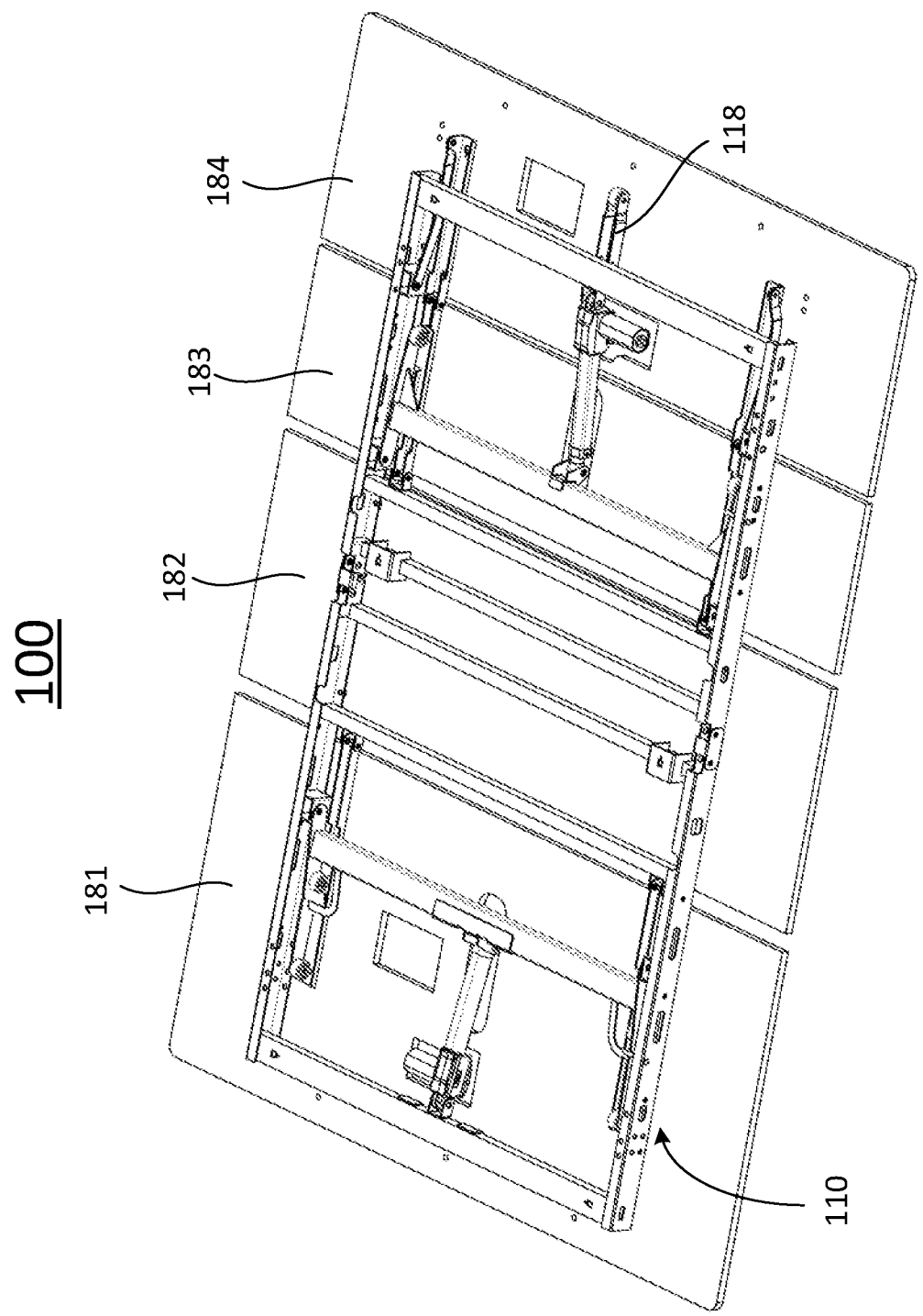
FIG. 7 shows schematically a rear perspective view of the adjustable bed shown in FIG. 1. The adjustable bed is in the flat state.

In operation, when the motor member 146 drives the activation rod 148 to expand, the expansion of the activation rod 148 pushes the back lifting bracket 141 to rotate in an upward rotation direction. As a result, the back lifting wheel/roller 144 on the free end of each swing arm 143 is sliding along the sliding slot 122 of the back support bar 121 and pushes the back support bar 121 to rotate in the upward rotation direction accordingly, which lifts the back platform 181 in a desired position/angle, where the bed is in the adjusting/lifting state, as shown in FIGS. 4-5. Otherwise, when the motor member 146 drives the activation rod 148 to retract, the retraction of the activation rod 148 results in the back lifting bracket 141 to rotate in a downward rotation direction due to gravity. As a result, the back lifting wheel/roller 144 on the free end of each swing arm 143 is sliding along the sliding slot 122 of the back support bar 121 and the back support bar 121 rotates in the downward rotation direction accordingly, which lowers the back platform 181 in a desired position/angle, or in a flat state, as shown in FIG. 7. Accordingly, such a design of which the back lifting bracket 141 is arranged below the upper support bracket 120 and abuts against the upper support bracket 120 such that the back lifting wheel/roller 144 of the back lifting bracket 141 is received in and operably sliding on the sliding slot 122 of the back lifting support bar 121 for the back platform 181 makes the lifting process of the back platform 181 more smooth and stable.

The leg lifting assembly 150 comprises a leg lifting bracket 151 pivotally connected to the frame structure 110 and slidably coupled to the lower support bracket 130, and a leg lifting actuator 155 pivotally connected between the leg lifting bracket 151 and the frame structure 110 for operably driving the leg lifting bracket 151 to pivotally move in an upward rotating direction or a downward rotating direction relative to the frame structure 110.

The leg lifting bracket 151 comprises a middle bar 152 and a pair of swing arms 153. The pair of swing arms 153 is transversely spaced and rigidly connected to ends of the transversely extending middle bar 152 in an H-shaped form. Each of the pair of swing arms 153 has a first end portion and an opposite, second end portion. The first end portion of each swing arm 153 is pivotally mounted to a respective side rail 111 of the frame structure 110. The second end portion of the swing arms is equipped with a leg lifting wheel/roller 154, which is operably slidable along the sliding slot 122 of the thigh support bar 131 of the lower support bracket 130. In addition, each of the pair of swing arms 153 may be reinforced by a reinforcing piece rigidly connected to the middle bar 152 and the swing arm 153.

The leg lifting actuator 155 comprises a motor member 156, an outer tube 157 extending from the motor member, an activation rod 158 received in the outer tube 157, engaged with the motor member 156 and configured to be telescopically movable relative to the outer tube 157 according to a direction of motor rotation. In one embodiment, the motor member 157 is pivotally connected to the lower rail 113 of the frame structure 110, and the activation rod 158 has a distal end portion pivotally connected to the middle bar 152 of the leg lifting bracket 151, via a bracket 152a mounted of the middle bar 152. In another embodiment, the motor member 146 is pivotally connected to the middle bar 152 of the leg lifting bracket 151, and the activation rod 158 has a distal end portion pivotally connected to the lower rail 113 of the frame structure 110.

In operation, when the motor member 156 drives the activation rod 158 to expand, the expansion of the activation rod 158 pushes the leg lifting bracket 151 to rotate in an upward rotation direction. As a result, the leg lifting wheel/roller 154 on the free end of each swing arm 153 is sliding along the sliding slot 132 of the thigh support bar 131 and pushes the thigh support bar 131 to rotate in the upward rotation direction accordingly, and the rotation of the thigh support bar 131 in the upward rotation direction in turn pulls the leg support bar 133 and the limit bar 135 to move accordingly, which lifts the thigh platform 183 and leg platform 184 in a desired position/angle, where the bed is in the adjusting/lifting state, as shown in FIGS. 4-5. Otherwise, when the motor member 156 drives the activation rod 158 to retract, the retraction of the activation rod 158 results in the leg lifting bracket 151 to rotate in a downward rotation direction due to the gravity. As a result, the leg lifting wheel/roller 154 on the free end of each swing arm 153 is sliding along the sliding slot 132 of the thigh support bar 131 and the thigh support bar 131 rotates in the downward rotation direction accordingly, and the rotation of the thigh support bar 131 in the downward rotation direction in turn pushes the leg support bar 133 and the limit bar 135 to move accordingly, which lowers the thigh platform 183 and the leg platform 184 in a desired position/angle, or in a flat state, as shown in FIG. 7. When the thigh platform 183 and the leg platform 184 are in the flat state, the leg platform 184 abuts against an auxiliary support bar 118 horizontally extended from the lower rail 113 of the frame structure 110. In other words, the auxiliary support bar 118 provides additional support to the leg platform 184 when it is in the flat state. Similarly, such a design of which the leg lifting bracket 151 is arranged below the lower support bracket 130 and abuts against the lower support bracket 130 such that the leg lifting wheel/roller 154 of the leg lifting bracket 151 is received in and operably sliding on the sliding slot 132 of the thigh lift support bar 131 for the thigh platform 183 and the leg platform 184 makes the lifting process of the thigh platform 183 and the leg platform 184 more smooth and stable.

Figure 8:
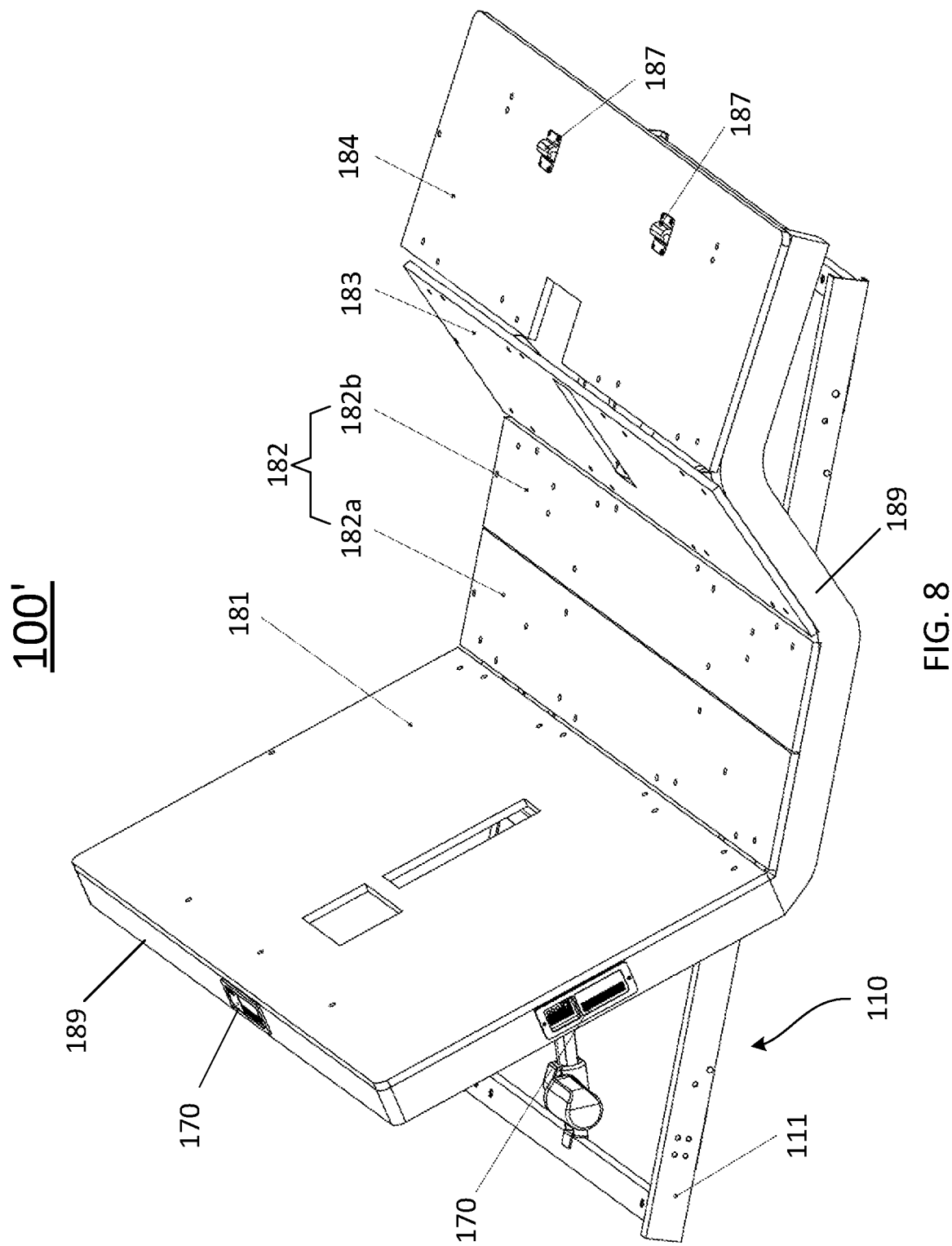
FIG. 8 shows schematically a front perspective view of an adjustable bed according to another embodiment of the invention. The adjustable bed is in an adjusting/lifting state.

Referring to FIG. 8, another embodiment of the adjustable bed 100' is shown, which is structurally similar to the adjustable bed 100, except the adjustable bed 100' further comprises an aromatherapy system 170 attached onto the one or more platforms 181-184 for producing desired fragrance in a surrounding space of the adjustable bed so as to promote health and well-being of a user. Additionally, in this exemplary embodiment, the seat platform 182 includes two boards 182a and 182b mounted on the side rails 111 of the frame structure 110.

In some embodiments, the aromatherapy system is an electric aromatherapy system comprising one or more aromatherapy devices 170. For example, as shown in FIG. 8 three aromatherapy devices 170 are employed and attached onto the back platform 181. It should be noted that other number of the aromatherapy devices 170 can also be utilized to practice the invention. In addition, the aromatherapy devices 170 can also be attached onto other platforms, or the frame structure 110. In addition, as shown in FIG. 8, the edges of the plurality of platforms 181-184 are provided with side boards 189 for better appearance.

In some embodiments, each aromatherapy device is configured to produce a fragrance when said aromatherapy device is turned on. The fragrance is identical to or different from that produced by other aromatherapy device of the one or more aromatherapy devices.

In some embodiments, each aromatherapy device has one or more working modes. The one or more working modes comprises a first working mode in which said aromatherapy device is turned on or turned off based on the user's instruction; a second working mode in which said aromatherapy device is turned on for a first period of time (e.g., 1 minute), and then turned off; and a third working mode in which said aromatherapy device is turned on for a second period of time (e.g., 1 minute) regularly in each and every third period of time (e.g., each and every 2 hours).

In some embodiments, each aromatherapy device 170 can be individually or cooperatively controlled to operate in one of the one or more working modes by a remote control or an APP.

Figure 9:
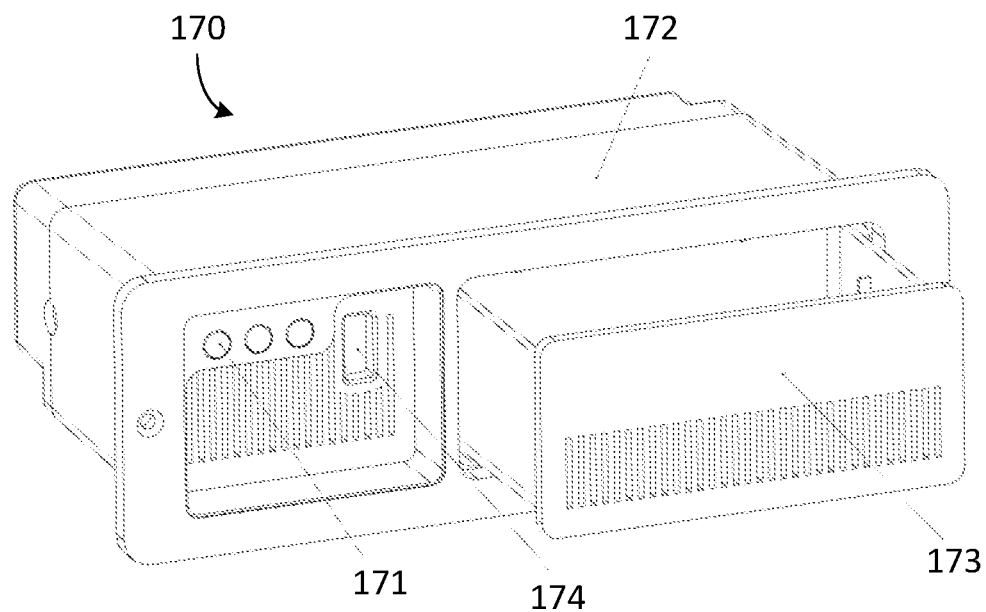
FIG. 9 shows schematically a front perspective view of an aromatherapy device according to one embodiment of the invention.

In one embodiment shown in FIG. 9, each aromatherapy device 170 comprises a container 173 for containing an aromatic substance; a diffuser coupled to the container 173 for operably heating the aromatic substance therein so as to produce the fragrance; and one or more indicators 171 with each indicator for indicating one of the one or more working modes of said aromatherapy device 170. Each aromatherapy device 170 also comprises a housing 172 for accommodating the container 173 and the indicators 171. The container 173 is detachable from the housing 172. In addition, each aromatherapy device 170 includes one or more USB port 174. According to the invention, each aromatherapy device 170 can contain an aromatic substance that is identical to or different from that of the aromatherapy devices 170.

The aromatic substance can be a substance extracted natural plants such as aromatic essential oils, or a chemically synthesized material. It is proven that aromatherapy using aromatic essential oils medicinally improves the health of the body, mind, and spirit, and has benefits including, but is not limited to, managing pain, improving sleep quality, reducing stress, agitation, and anxiety, soothing sore joints, treating headaches and migraines, and boosting immunity.

The capability of producing different fragrances from the one or more aromatherapy devices 170 and the controllability of the one or more aromatherapy devices 170 have particular therapeutic benefits for the user. For example, during wake up time, one aromatherapy devices 170 can be configured to produce a fresh air fragrance, while during a sleep time, the other aromatherapy devices 170 can be configured to produce a fragrance improving sleep quality of the user.

In one embodiment, the adjustable bed further comprises at least one massage assembly for providing massage effects to the user.

Figure 3:
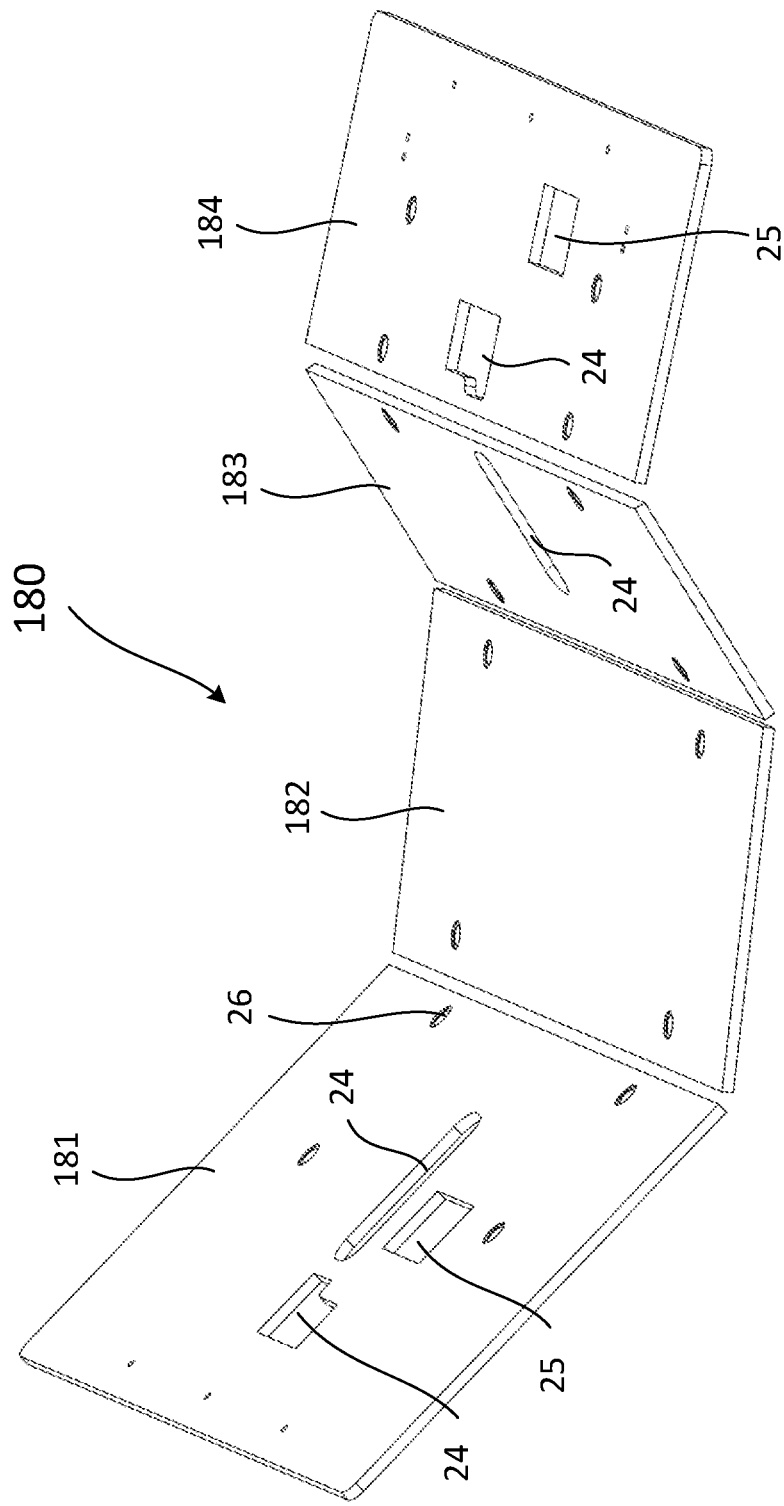
FIG. 3 shows schematically and partially a front perspective view of the adjustable bed shown in FIG. 1.

In addition, the adjustable bed 100/100' may further include at least one massage assembly 190 for providing massage effects to a user of the bed. The massage assembly 190 can be disposed in the massage receiving slot 25 on the back platform 181, as shown in FIG. 3.

Figure 10:
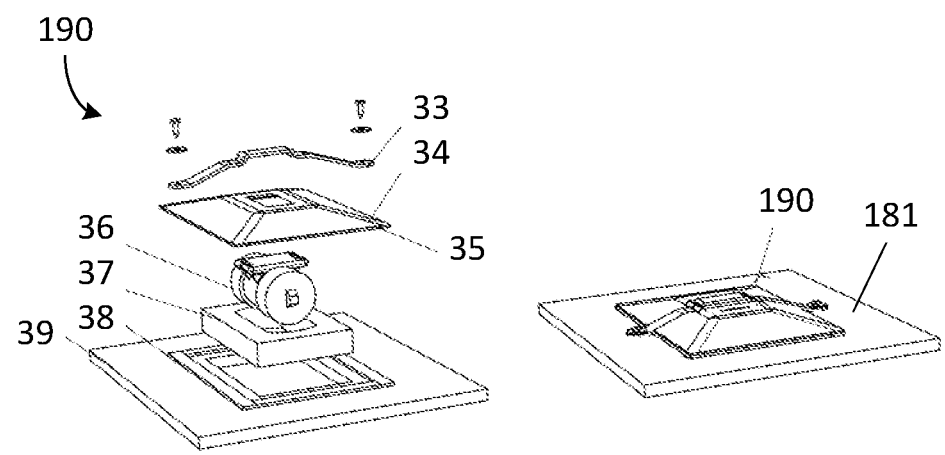
FIG. 10 shows schematically an exploded view and a perspective view of a massage assembly according to one embodiment of the invention.

As shown in FIG. 10, the massage assembly 190 includes a massage motor 36, an elastic belt 33, a massage motor cover 34, a velcro loop surface 35, a foam house 37, a velcro hook surface 38, and a plywood decking 39. The velcro loop surface 35 and the massage motor cover 34 are connected. A side of the massage motor 36 passes through an opening of the massage motor cover 34, and the elastic belt 33 passes through the side of the massage motor 36 (the side of the massage motor 36 has a small opening for the elastic belt to pass through) to connect the components as a whole. Further, the velcro hook surface 38 is fixed onto the plywood decking 39, which may be done by a nail or any other connecting means not limited thereto. The foam house 37 is placed inside a hole of the plywood decking 39, and the massage motor 36 as assembled above is placed inside a hole of the foam house 37 so that the velcro loop surface 35 and the velcro hook surface 38 are fit together. Finally, the massage motor 36 is fastened onto the plywood decking 39, e.g., via a pair of screws and a pair of washers. The massage motor 36 can be easily replaced by simply removing the elastic belt 33 from the side of the massage motor 36 and separating the velcro surfaces.

Further, as shown in FIG. 8, the leg platform 184 is equipped with two mattress retainer bar holder 187 for retaining the mattress on the plurality of platforms 181-184.

Figure 11:
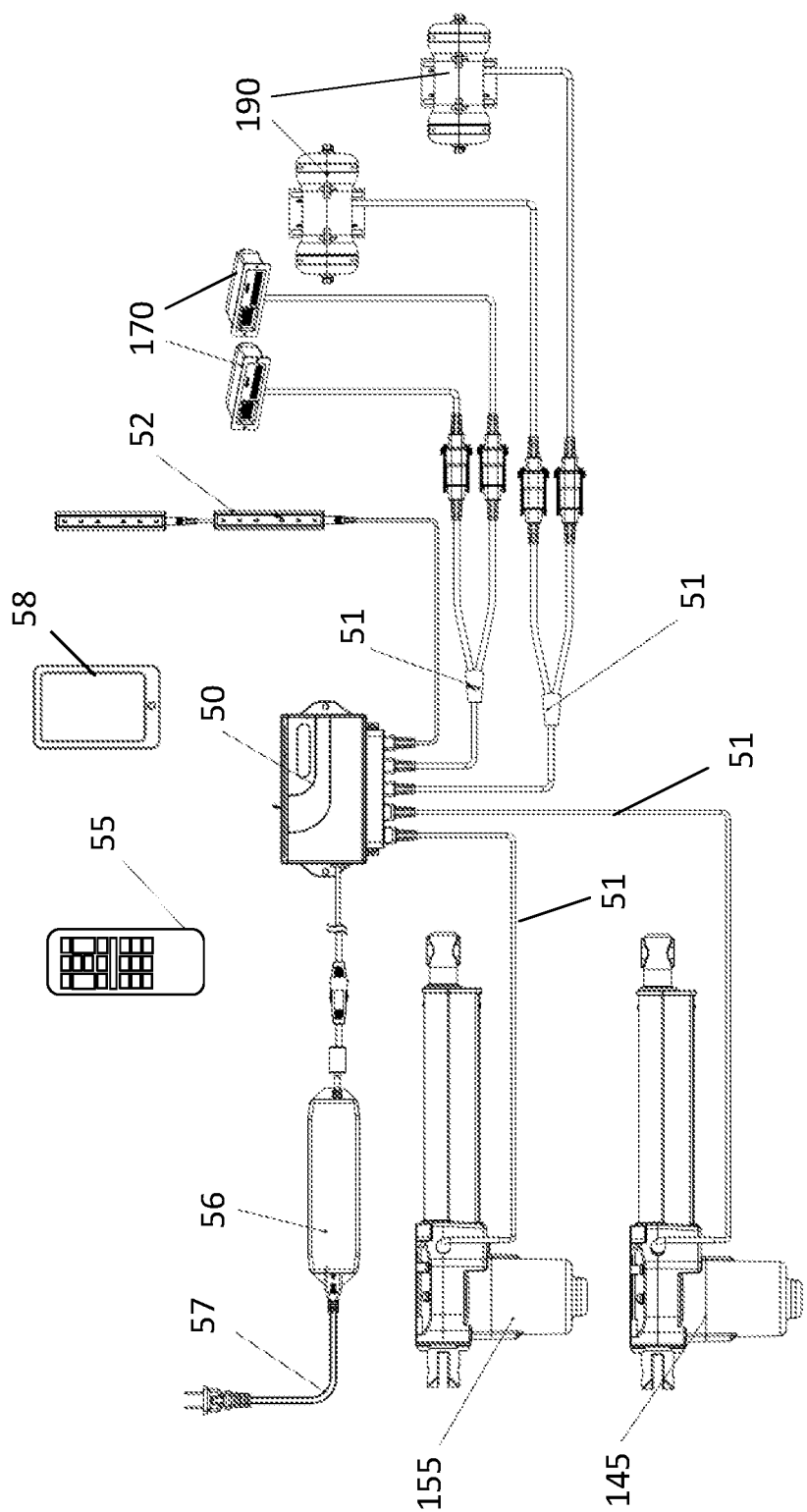
FIG. 11 shows schematically a control system according to one embodiment of the invention.

The adjustable bed further includes a controlling system having a controller 50, which is shown in FIG. 11 according to one embodiment of the invention. The controller 50 is configured to control operations of the back lifting actuator (motor) 145, the leg lifting actuator (motor) 155, the aromatherapy system 170, and the massage assembly 190, respectively, so as to lift individually or cooperatively the head lifting platform 181, the thigh platform 183, and the leg platform 184 in desired positions, to produce the fragrance in the surrounding space of the adjustable bed, and to provide the massage effects to the user. In one embodiment shown in FIG. 11, the control system includes a power cord 57, a power supply 56, a control box (controller) 50, a plurality of connecting cables 51, and LED lights 52. The control box 50 is powered by the power supply 56 which is in turn connected to any power source via the power cord 57. The back lifting motor 145 and the leg lifting motor 155 are connected to the control box 50 via the plurality of connection cables 51. In this way, the user can adjust the bed position via a remote controller 55 or an APP installed in a mobile device such as a smart phone 58. Alternatively, LED lights 52 can be employed to indicate the working conditions of the back lifting motor 145 and the leg lifting motor 155.

FIG. 11 shows one exemplary embodiment of the controlling system with the controller 50 wiredly connected to the back lifting actuator (motor) 145, the leg lifting actuator (motor) 155, the aromatherapy system 170, the massage assembly 190, and/or LED lights 52 through the connecting cables 51. In other embodiments, these connections of the controller 50 connected to t the back lifting actuator (motor) 145, the leg lifting actuator (motor) 155, the aromatherapy system 170, the massage assembly 190, and/or LED lights 52 are wireless connections through the Internet, WiFi®, Bluetooth®, a cellular network, and/or a mobile network.

According to the invention, when back lifting assembly 140 and the leg lifting assembly 150 are in their retraction positions, the upper support bracket 120 and the lower support bracket 130 are in a horizontal state, such that the platforms 180 are in the flat state, as shown in FIG. 7. When the back lifting assembly 140 and the leg lifting assembly 150 are in their expansion positions, the upper support bracket 120 and the lower support bracket 130 are in an adjusting state, such that the platforms 180 are lifted in the adjusting state, which is convenient for some daily entertainment activities, as shown in FIG. 4. Each of back lifting assembly 140 and the leg lifting assembly 150 can be individually controlled so that the positions/angles of the back platform 181, the thigh platform 183 and the leg platform 184 can be individually adjusted according to user's preference. In addition, the bed has therapeutic functions to promote health and well-being of a user Further, without using hinging connections, the platforms can be individually installed on the support bars/frames, thereby making the installation, transportation, and/or maintenance of the adjustable bed easier. The invention also solves the safety issues of an adjustable bed with hinged platforms in the prior art.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. An adjustable bed, comprising:
a frame structure;
an upper support bracket and a lower support bracket pivotally connected to the frame structure;
a plurality of platforms disposed on the frame structure and supported by the upper support bracket and the lower support bracket without using hinging means; and
an adjustable assembly coupled with the frame structure and the upper support bracket and the lower support bracket for operably adjusting one or more of the plurality of platforms in desired positions,
wherein the frame structure comprises:
a pair of side rails transversely spaced and longitudinally extended and being parallel to each other, each side rail having an upper end and opposite, lower end;
an upper rail and a lower rail longitudinally spaced and transversely extended, two ends of the upper rail connected to the upper ends of the pair of side rails and two ends of the lower rail connected to the lower ends of the pair of side rails such that the upper rail and the lower rail are parallel to each other; and
an upper reinforcement beam and a lower reinforcement beam directly and fixedly connected to each of the pair of side rails at positons such that the upper reinforcement beam is positioned between the upper rails and the lower reinforcement beam, while the lower reinforcement beam is positioned between the upper reinforcement beam and the lower rail;
wherein the pair of side rails, the upper rail, the lower rail, the upper reinforcement beam and the lower reinforcement beam of the frame structure are co-planar in a rectangle form;
wherein the upper support bracket comprises a pair of back support bars pivotally connected to the upper reinforcement beam;
wherein the lower support bracket comprises a pair of lower support structures, each lower support structure comprising a thigh support bar pivotally connected to the lower reinforcement beam, and a leg support bar pivotally connected to the thigh support bar, and a limit bar pivotally connected to the leg support bar and a respective side rail of the pair of side rails; and
wherein the plurality of platforms comprises:
a back platform mounted on the back support bar of the back support bar bracket;
a seat platform mounted on the side rails of the frame structure;
a thigh platform mounted on the thigh support bar of the leg support bracket; and
a leg platform mounted on the leg support bar of the leg support bracket;
wherein the back platform, the seat platform, the thigh platform and the leg platform are not hinged to one another.

2. The adjustable bed of claim 1, wherein each of the back support bar, the thigh support bar, and the leg support bar has one or more mounting holes for mounting the back platform, the thigh platform and the leg platform, respectively.

3. An adjustable bed, comprising:
a frame structure;
an upper support bracket and a lower support bracket pivotally connected to the frame structure;
a plurality of platforms disposed on the frame structure and supported by the upper support bracket and the lower support bracket without using hinging means; and
an adjustable assembly coupled with the frame structure and the upper support bracket and the lower support bracket for operably adjusting one or more of the plurality of platforms in desired positions,
wherein the frame structure comprises:
a pair of side rails transversely spaced and longitudinally extended and being parallel to each other, each side rail having an upper end and opposite, lower end;
an upper rail and a lower rail longitudinally spaced and transversely extended, two ends of the upper rail connected to the upper ends of the pair of side rails and two ends of the lower rail connected to the lower ends of the pair of side rails such that the upper rail and the lower rail are parallel to each other; and
an upper reinforcement beam and a lower reinforcement beam directly and fixedly connected to each of the pair of side rails at positons such that the upper reinforcement beam is positioned between the upper rails and the lower reinforcement beam, while the lower reinforcement beam is positioned between the upper reinforcement beam and the lower rail;
wherein the pair of side rails, the upper rail, the lower rail, the upper reinforcement beam and the lower reinforcement beam of the frame structure are co-planar in a rectangle form;
wherein the upper support bracket comprises a pair of back support bars pivotally connected to the upper reinforcement beam;
wherein the lower support bracket comprises a pair of lower support structures, each lower support structure comprising a thigh support bar pivotally connected to the lower reinforcement beam, and a leg support bar pivotally connected to the thigh support bar, and a limit bar pivotally connected to the leg support bar and a respective side rail of the pair of side rails;

wherein each back support bar has a sliding slot formed thereunderneath; and wherein each thigh support bar has a sliding slot formed thereunderneath.

4. The adjustable bed of claim 3, wherein the adjustable assembly comprises:

a back lifting assembly comprising a back lifting bracket pivotally connected to the frame structure and slidably coupled to the upper support bracket, and a back lifting actuator pivotally connected between the back lifting bracket and the frame structure for operably driving the back lifting bracket to pivotally move in an upward rotating direction or a downward rotating direction relative to the frame structure; and a leg lifting assembly comprising a leg lifting bracket pivotally connected to the frame structure and slidably coupled to the lower support bracket, and a leg lifting actuator pivotally connected between the leg lifting bracket and the frame structure for operably driving the leg lifting bracket to pivotally move in an upward rotating direction or a downward rotating direction relative to the frame structure.

5. The adjustable bed of claim 4, wherein the back lifting bracket comprises a middle bar and a pair of swing arms, wherein the pair of swing arms is transversely spaced and rigidly connected to ends of the transversely extending middle bar, and each of the pair of swing arms has a first end portion and an opposite, second end portion, wherein the first end portion of each swing arm is pivotally mounted to a respective side rail of the frame structure; and the back lifting actuator comprises a motor member, an outer tube extending from the motor member, an activation rod received in the outer tube, engaged with the motor member and configured to be telescopically movable relative to the outer tube according to a direction of motor rotation, wherein the motor member is pivotally connected to the upper rail of the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the upper rail of the frame structure.

6. The adjustable bed of claim 5, wherein the swing arms are in an arc-shaped design.

7. The adjustable bed of claim 5, wherein the second end portion of the swing arms is equipped with a back lifting wheel, which is operably slidable along the sliding slot of the back support bar of the upper support bracket.

8. The adjustable bed of claim 4, wherein the leg lifting bracket comprises a middle bar and a pair of swing arms, wherein the pair of swing arms is transversely spaced and rigidly connected to ends of the transversely extending middle bar, and each of the pair of swing arms has a first end portion and an opposite, second end portion, wherein the first end portion of each swing arm is pivotally mounted to a respective side rail of the frame structure; and the leg lifting actuator comprises a motor member, an outer tube extending from the motor member, an activation rod received in the outer tube, engaged with the motor member and configured to be telescopically movable relative to the outer tube according to a direction of motor rotation, wherein the motor member is pivotally connected to the lower rail of the frame structure, and the activation rod has a distal end portion pivotally connected to the middle bar of the leg lifting bracket, or wherein the motor member is pivotally connected to the middle bar of the leg lifting bracket, and the activation rod has a distal end portion pivotally connected to the lower rail of the frame structure.

9. The adjustable bed of claim 8, wherein the second end portion of the swing arms is equipped with a leg lifting wheel, which is operably slidable along the sliding slot of the thigh support bar of the lower support bracket.

10. The adjustable bed of claim 3, wherein each of the pair of side rails comprises two parts that are foldably connected to each other by a folding mechanism.

11. The adjustable bed of claim 3, further comprising an aromatherapy system attached onto the one or more platforms for producing desired fragrance in a surrounding space of the adjustable bed so as to promote health and well-being of a user.

12. The adjustable bed of claim 11, wherein the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

13. An adjustable bed, comprising:

a frame structure;

an upper support bracket and a lower support bracket pivotally connected to the frame structure;

a plurality of platforms disposed on the frame structure and supported by the upper support bracket and the lower support bracket without using hinging means;

an adjustable assembly coupled with the frame structure and the upper support bracket and the lower support bracket for operably adjusting one or more of the plurality of platforms in desired positions; and an aromatherapy system attached onto the one or more platforms for producing desired fragrance in a surrounding space of the adjustable bed so as to promote health and well-being of a user, wherein the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices; and wherein each aromatherapy device has one or more working modes, wherein the one or more working modes comprises:

a first working mode in which said aromatherapy device is turned on or turned off based on the user's instruction;

a second working mode in which said aromatherapy device is turned on for a first period of time, and then turned off; and a third working mode in which said aromatherapy device is turned on for a second period of time regularly in a third period of time.

14. The adjustable bed of claim 13, wherein each aromatherapy device comprises a container for containing an aromatic substance;

a diffuser coupled to the container for operably heating the aromatic substance therein so as to produce the fragrance; and one or more indicators, each indicator for indicating one of the one or more working modes of said aromatherapy device.

15. The adjustable bed of claim 14, wherein each aromatherapy device is controllable to operate in one of the one or more working modes by a remote control or an APP.

16. The adjustable bed of claim 13, further comprising at least one massage assembly for providing massage effects to the user.

* * * * *